United States Patent [19]
Stein et al.

[11] Patent Number: 6,030,955
[45] Date of Patent: Feb. 29, 2000

[54] METHODS OF AFFECTING INTRACELLULAR PHOSPHORYLATION OF TYROSINE USING PHOSPHOROTHIOATE OLIGONUCLEOTIDES, AND ANTIANGIOGENIC AND ANTIPROLIFERATIVE USES THEREOF

[75] Inventors: Cy Stein, New City, N.Y.; Patricia Rockwell, West Redding, Conn.

[73] Assignee: The Trustees of Columbia University in The City of New York and ImClone Systems, Inc., New York, N.Y.

[21] Appl. No.: 08/619,407

[22] Filed: Mar. 21, 1996

[51] Int. Cl.[7] .......................... A01N 43/04; A61K 31/705
[52] U.S. Cl. ................................. 514/44; 514/43
[58] Field of Search ......................... 514/43, 44

[56] References Cited

FOREIGN PATENT DOCUMENTS

| 9410202 | 5/1994 | WIPO . |
| 9411499 | 5/1994 | WIPO . |

OTHER PUBLICATIONS

Abstract to Sakano et al. of JP 94–320712, Dec. 22, 1994.

Stedman's Medical Dictionary, 24th Edition, pp. 777 and 1254, Feb. 1983.

Guvakova, M.A., et al., "Phosphorothioate Oligodeoxynucleotides Bind to Basic Fibroblast Growth Factor, Inhibit Its Binding to Cell Surface Receptors, and Remove It from Low Affinity Binding Sites on Extracellular Matrix." *J. Biol. Chem.* 270: 2620–2627 (1995).

Khalad, Z., et al., "Effects of Suramin–related and Other Clinically Therapeutic Polyanions on Protein Kinase C Activity[1]." *Clin. Cancer Res. 1*: 113–122 (1995).

Millauer, B., et al., "Glioblastoma growth inhibited in vivo by a dominant–negative F1k–1 mutant." *Nature (Lond) 367*: 576–579 (1994).

Yakubov, L., et al., "Oligodeoxynucleotides Interact with Recombinant CD4 at Multiple Sites*." *J. Biol. Chem. 268*: 18818–18823 (1993).

*Primary Examiner*—Raymond Henley, III
*Assistant Examiner*—Dwayne C. Jones
*Attorney, Agent, or Firm*—John P. White; Cooper & Dunham LLP

[57] ABSTRACT

The present invention provides methods of stimulating or inhibiting intracellular phosphorylation of tyrosine by a heparin-binding receptor which comprises contacting a cell having on its surface the heparin-binding receptor with a phosphorothioate oligonucleotide moiety of suitable length and base composition, such phosphorothioate oligonucleotide moiety being present in an effective amount. The invention further provides a method of inhibiting the formation of blood vessels in a subject which comprises administering to the subject an amount of a phosphorothioate oligonucleotide moiety of suitable length and base composition. The invention also provides a method of inhibiting proliferation of cells having a malignant phenotype in a subject which comprises administering to the subject an amount of a phosphorothioate oligonucleotide moiety of suitable length and base composition.

3 Claims, 12 Drawing Sheets

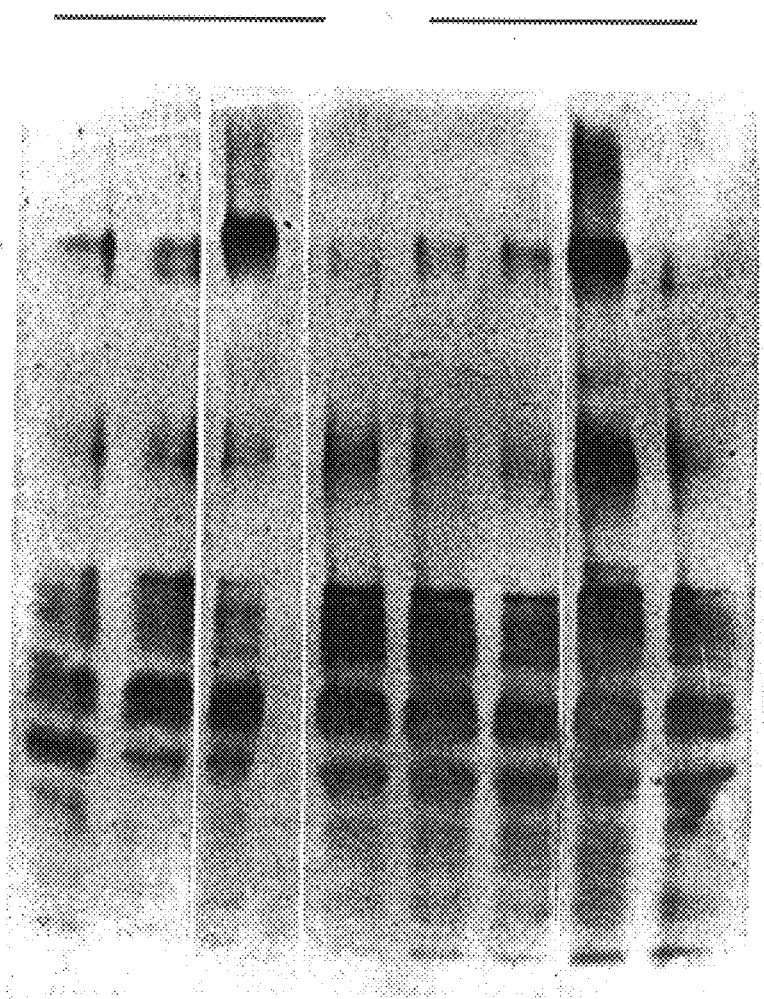

EGFR→

1  2  3  4

Probe:     α Ptyr

EGFR→

1  2  3  4  5

Probe:     α EGFR

FIG. 3A 170 kD band----
1 2 3 4
Probe: α Ptyr
FIG. 3B
1 2 3 4
Probe: α PTyr FIG. 4C
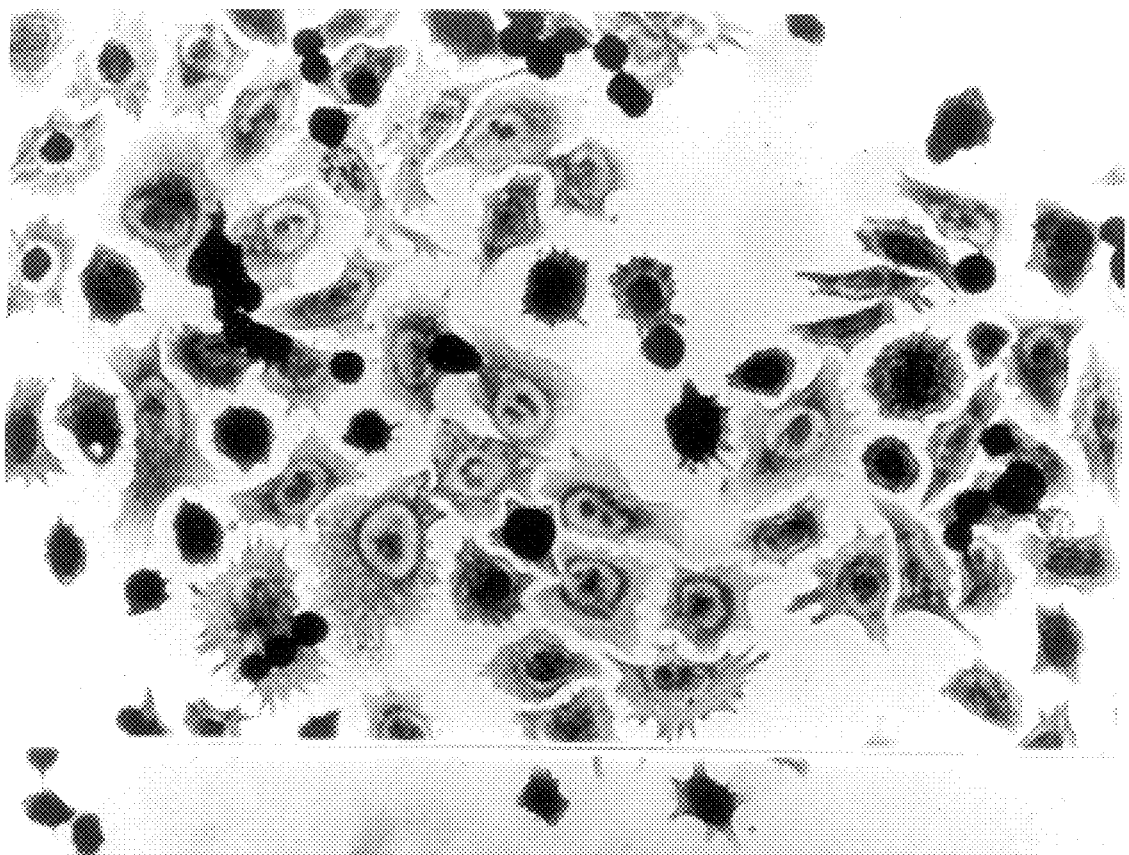
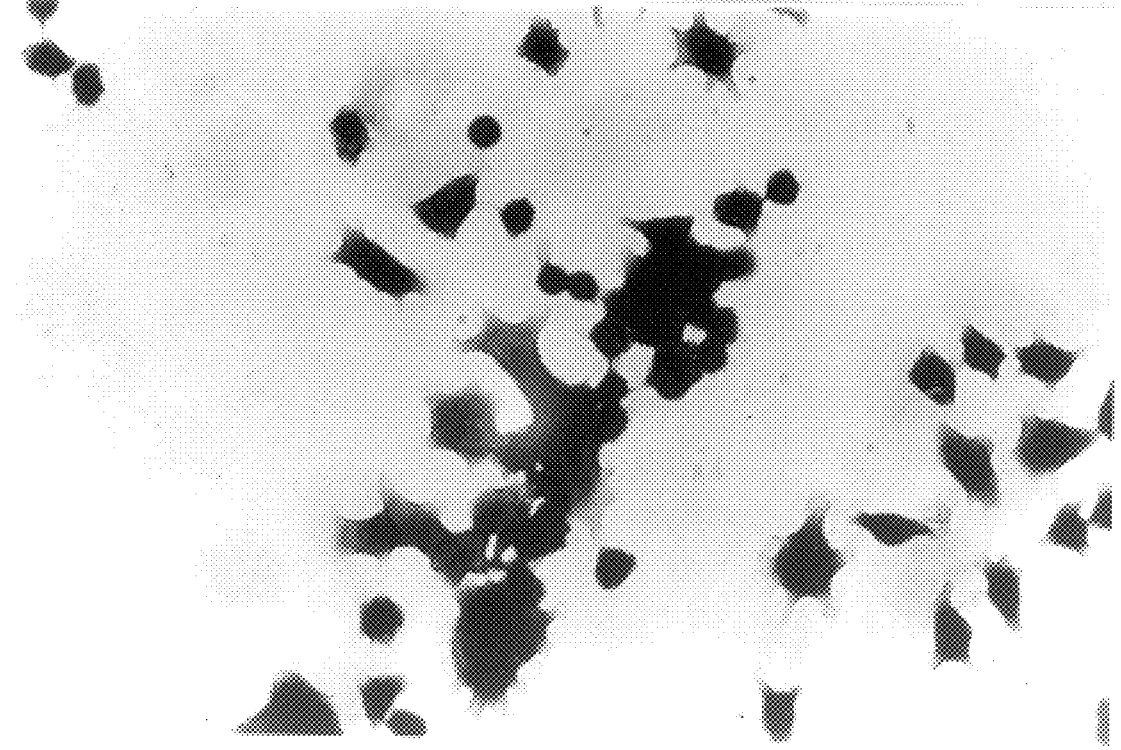
FIG. 4D

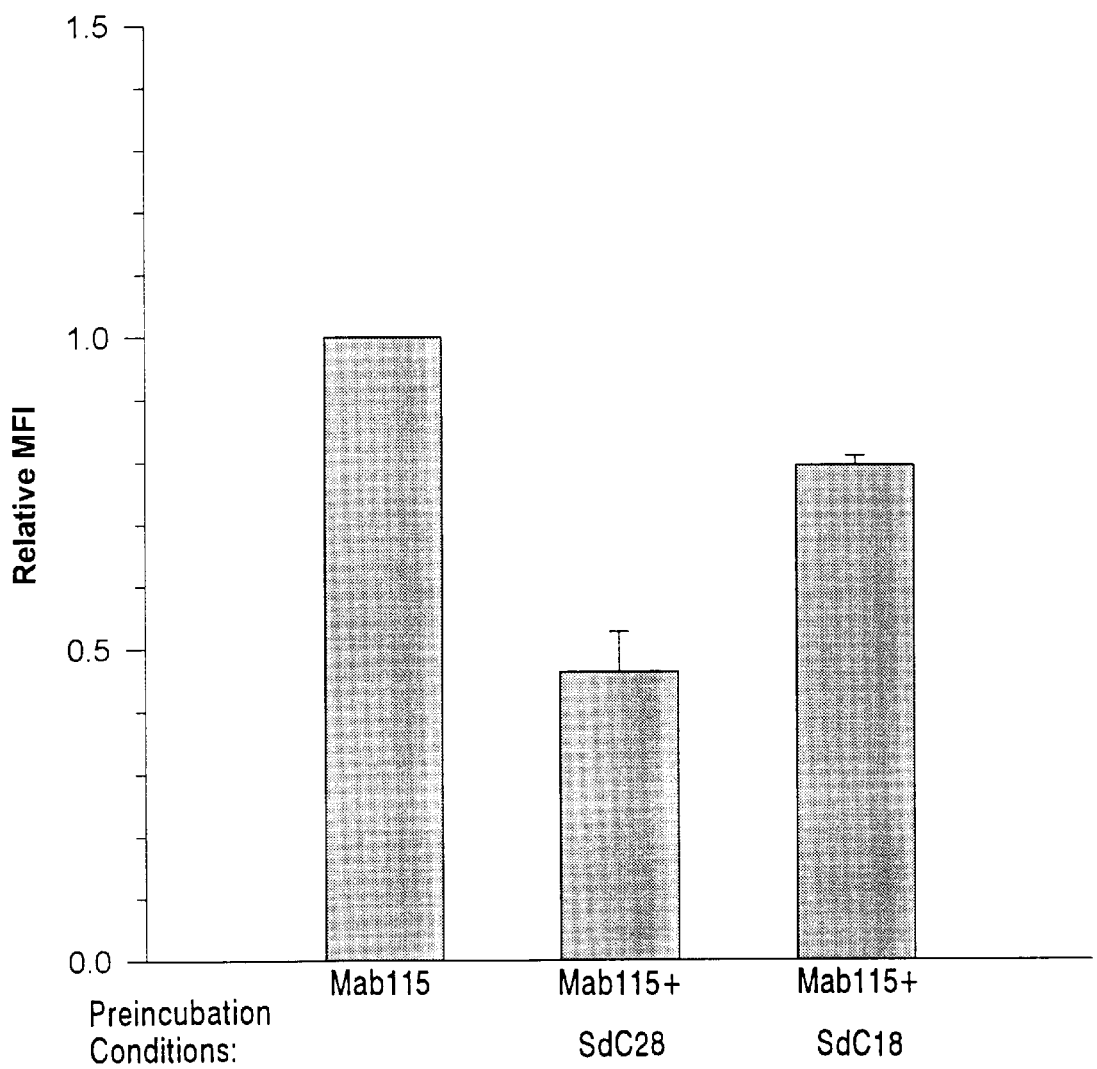

METHODS OF AFFECTING INTRACELLULAR PHOSPHORYLATION OF TYROSINE USING PHOSPHOROTHIOATE OLIGONUCLEOTIDES, AND ANTIANGIOGENIC AND ANTIPROLIFERATIVE USES THEREOF

Throughout this application, various publications are referenced by Arabic numerals in brackets. Full citations for these publications may be found at the end of the specification immediately preceding the claims. The disclosures of these publications are hereby incorporated by reference in their entireties into this application to more fully describe the state of the art to which this invention pertains.

BACKGROUND OF THE INVENTION

Antisense technology has been exploited as a potential therapeutic approach for the treatment of a variety of pathological disorders including AIDS and cancer. This strategy is based on the premise that sequence-specific oligodeoxynucleotides can serve as inhibitors of gene expression by a direct interaction with their appropriate mRNA or DNA targets. To improve the effectiveness of antisense oligodeoxynucleotides as therapeutic reagents, a great deal of effort has been placed on the use of structurally modified oligomers. In particular, phosphorothioate oligodeoxynucleotides have been widely used antisense reagents in which a sulfur atom is substituted for one of the nonbridging oxygen atoms bound to phosphorous. Phosphorothioates offer several advantages to phosphodiester oligodeoxynucleotides, including greater serum stability and nuclease resistance. Moreover, phosphorothioates hybridize well to target mRNA and elicit RNase H activity which cleaves the mRNA of the mRNA-DNA duplex. However, the polyanionic nature of phosphorothioate oligodeoxynucleotides has led, in some cases, to uncertainty regarding the extent to which observed biological effects stem from an antisense mechanism. Recent evidence implicating phosphorothioate oligodeoxynucleotides in nonsequence-specific protein interactions, i.e., aptameric binding, has raised questions regarding their specificity for target mRNA[1].

Oligodeoxynucleotides interact with proteins in a complex manner that is dependent upon charge, length or concentration [2,3,4]. The binding of oligodeoxynucleotides to protein may result in protein-oligomer complexes that may confer undesirable consequences for normal cellular physiology. For example, phosphorothioate oligodeoxynucleotides have been shown to form complexes with the heparin-binding growth factors, basic fibroblast growth factor (bFGF), platelet-derived growth factor (PDGF), vascular endothelial growth factor (VEGF) (but not epidermal growth factor (EGF) which has a poor affinity for heparin) [5]. In the case of bFGF, binding of the phosphorothioate oligomer is augmented when four contiguous guanosine residues are present. Studies with the tyrosine kinase receptor, bcr-abl, have shown that direct interaction of an oligomer with the protein leads to a reduction in the phosphorylation levels of both receptor and of downstream signaling proteins [6].

This application sets forth several in vitro assays performed to show that phosphorothioate oligodeoxynucleotides of defined sequence and length interact with two cell surface expressed protein tyrosine kinase receptors, flk-1 and EGFR. These receptors play an important functional role in normal and pathological cellular events. The results show that oligodeoxynucleotides bound receptors differentially and elicited alterations in cellular tyrosine phosphorylation patterns in the presence and absence of their cognate ligands. Treatment of cultured tumor cells with phosphorothioate oligodeoxynucleotides resulted in gross changes in cellular morphology, whereas the in vivo administration of one nonspecific phosphorothioate oligodeoxynucleotide significantly inhibited growth of GBM-18 cells in mouse xenografts. These results highlight the biological potency and demonstrate the potential therapeutic efficacy of non-sequence specific phosphorothioate oligodeoxynucleotides.

SUMMARY OF THE INVENTION

The present invention provides a method of stimulating intracellular phosphorylation of tyrosine by a heparin-binding receptor which comprises contacting a cell having on its surface the heparin-binding receptor with a phosphorothioate oligonucleotide moiety of suitable length and base composition in the absence of any ligand capable of binding to the heparin-binding receptor, such phosphorothioate oligonucleotide moiety being present in an amount effective to activate the heparin-binding receptor and thereby stimulate intracellular phosphorylation of tyrosine.

The present invention further provides a method of inhibiting intracellular phosphorylation of tyrosine by a heparin-binding receptor which comprises contacting a cell having on its surface the heparin-binding receptor with a phosphorothioate oligonucleotide moiety of suitable length and base composition in the presence of a ligand capable of binding to the heparin-binding receptor, such phosphorothioate oligonucleotide moiety being present in an amount effective to inhibit the ligand from binding to the heparin-binding receptor and thereby inhibit intracellular phosphorylation of tyrosine.

The present invention also provides a method of inhibiting the formation of blood vessels in a subject which comprises administering to the subject an amount of a phosphorothioate oligonucleotide moiety of suitable length and base composition effective to inhibit VEGF molecules from binding to VEGF receptors on the surface of cells in the subject and thereby inhibit intracellular phosphorylation of tyrosine in the subject.

Further, the present invention provides a method of inhibiting proliferation of cells having a malignant phenotype in a subject which comprises administering to the subject an amount of a phosphorothioate oligonucleotide moiety of suitable length and base composition effective to inhibit EGF molecules from binding to EGF receptors on the surface of cells in the subject and thereby inhibit intracellular phosphorylation of tyrosine in the subject.

BRIEF DESCRIPTION OF THE FIGURES

FIG. 1: Effect of phosphorothioate oligodeoxynucleotides on VEGF induced activation of the flk-1/fms receptor. Each lane represents the phosphorylated receptor immunoprecipitated from an equal number of C441 cells prebound with 2 $\mu$M oligodeoxynucleotide and stimulated with 20 ng/ml VEGF for 15 minutes at room temperature. Cells were either washed with cold PBS (lanes 1–4) or unwashed (lanes 5–8) prior to the addition of ligand. The level of flk-1/fms activation induced by VEGF is shown for cells preincubated with 2 $\mu$M of the oligodeoxynucleotides SdC28 (lanes 1 and 5), #2 (lane 2 and 6) or without oligodeoxynucleotide (lanes 3 and 7) relative to unstimulated controls (lanes 4 and 8).

FIG. 3A: Effect of oligodeoxynucleotides on DU145 cells. Phosphoprotein patterns obtained from lysates immunoprecipitated with an anti-flk-1 MAb DC101 from cells incubated at room temperature for 15 minutes in the absence (lane 1) and presence (lane 2) of 2 μM oligo SdC28, 2 μM oligo #2 (lane 3), or 10 ng/ml EGF (lane 4).

FIG. 3B: Oligodeoxynucleotide stimulation of EGFR phosphorylation. Blots from FIG. 3A were stripped and reprobed with an anti-human EGFR polyclonal antibody (UBI) raised against a recombinant receptor fusion protein. A receptor band is seen that corresponds to the 170 kDa phosphorylated protein immunoprecipitated from cells incubated with oligodeoxynucleotide #2 (lane 3) and EGF (lane 4).

FIGS. 4A–4D: Oligodeoxynucleotide-induced changes in cell morphology. Cultures of KB cells are shown following a 72 hour incubation in the absence (FIG. 4A) and presence of 2 μM of the oligodeoxynucleotides SdC28 (FIG. 4B), #2T (FIG. 4C) and G6T12 (FIG. 4D). Morphological changes were detected by light microscopy of Giemsa stained cells as described in the Materials and Methods.

FIGS. 6A–B: FACS analysis of MAb binding to C441 cells preincubated with oligodeoxynucleotides of identical sequence but different length. Shown are the binding of MAbs 115 (FIG. 6A) and 73 (FIG. 6B) to cells prebound with either SdC28 or SdC18. Results are graphed and analyzed as described in the legend to FIGS. 5A–5C. MAb binding to oligodeoxynucleotide treated cells was significantly different from control values of binding to untreated cells ($p<0.05$).

DETAILED DESCRIPTION OF THE INVENTION

Figure 2A:
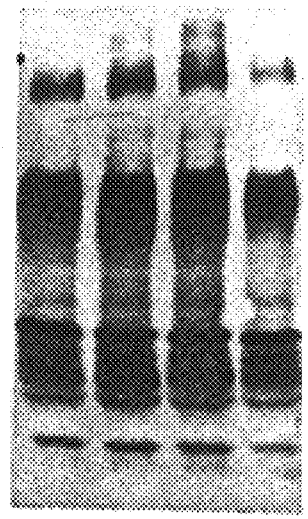
FIG. 2A: Effect of phosphorothioate oligodeoxynucleotides on EGFR activity in KB cells. Shown is oligodeoxynucleotide-induced phosphorylation of EGFR from total lysates of KB cells incubated for 30 minutes at room temperature with 2 μM of the oligodeoxynucleotides G6T12 (lane 1), #2T (lane 2), SdC28 (lane 3) or without oligodeoxynucleotide (lane 4).

The present invention provides a method of stimulating intracellular phosphorylation of tyrosine by a heparin-binding receptor which comprises contacting a cell having on its surface the heparin-binding receptor with a phosphorothioate oligonucleotide moiety of suitable length and base composition in the absence of any ligand capable of binding to the heparin-binding receptor, such phosphorothioate oligonucleotide moiety being present in an amount effective to activate the heparin-binding receptor and thereby stimulate intracellular phosphorylation of tyrosine.

The present invention further provides a method of inhibiting intracellular phosphorylation of tyrosine by a heparin-binding receptor which comprises contacting a cell having on its surface the heparin-binding receptor with a phosphorothioate oligonucleotide moiety of suitable length and base composition in the presence of a ligand capable of binding to the heparin-binding receptor, such phosphorothioate oligonucleotide moiety being present in an amount effective to inhibit the ligand from binding to the heparin-binding receptor and thereby inhibit intracellular phosphorylation of tyrosine.

As used herein, the phrase "an amount effective to inhibit the ligand from binding to the heparin-binding receptor and thereby inhibit intracellular phosphorylation of tyrosine" means that amount which is effective to inhibit the ligand from binding to the heparin-binding receptor and thereby inhibit intracellular phosphorylation of tyrosine. An effective amount depends on such factors as the type of cell contacted with the phosphorothioate oligonucleotide moiety, the concentration of ligand present, the number of receptors on the surface of the cell, the type of receptor, the phosphorothioate oligonucleotide moiety employed, and the duration of contact between the phosphorothioate oligonucleotide moiety and the cell. An effective amount can be determined by contacting a sample containing a predetermined number of cells with various concentrations of a phosphorothioate oligonucleotide moiety, monitoring the degree of tyrosine phosphorylation that occurs, and determining at which concentrations intracellular phosphorylation is inhibited.

Likewise, the phrase "an amount effective to activate the heparin-binding receptor and thereby stimulate intracellular phosphorylation of tyrosine" means that amount which is effective to stimulate the heparin-binding receptor and thereby stimulate intracellular phosphorylation of tyrosine. Such an effective amount depends on factors such as the type of cell contacted with the phosphorothioate oligonucleotide moiety, the type of receptor, the number of receptors on the surface of the cell, the phosphorothioate oligonucleotide moiety employed, and the duration of contact between the phosphorothioate oligonucleotide moiety and the cell. An effective amount can be determined by contacting a sample containing a predetermined number of cells with various concentrations of a phosphorothioate oligonucleotide moiety, monitoring the degree of tyrosine phosphorylation that occurs, and thereby determining at which concentrations intracellular tyrosine phosphorylation is stimulated.

A heparin-binding receptor for purposes of the subject invention is a cell receptor which is capable of binding to heparin. Heparin-binding receptors for which this invention is applicable include, but are not limited to, receptors for VEGF and receptors for EGF. Examples of VEGF receptors include, but are not limited to, flk-1 for mice and flk-1/KDR for humans. Other heparin-binding receptors are known in the art, and the invented method may be applied to such receptors.

Throughout this application, the following standard abbreviations are used to indicate specific nucleotides:

| C = Cytidine | A = Adenosine |
|---|---|
| T = Thymidine | G = Guanosine |

Examples of phosphorothioate oligonucleotide moieties include, but are not limited to, a phosphorothioate oligodeoxynucleotide, a phosphorodithioate, a chimeric oligonucleotide, an oligonucleotide homopolymer, a oligonucleotide heteropolymer, or a phosphorothioate oligonucleotide which is further linked to another chemical moiety.

In one embodiment the phosphorothioate oligonucleotide moiety comprises a phosphorothioate oligonucleotide. In another embodiment, the phosphorothioate oligonucleotide moiety comprises a phosphorothioate oligonucleotide linked to another chemical moiety. In a further embodiment, the phosphorothioate oligonucleotide of the phosphorothioate oligonucleotide moiety has a length of from about 8 to about 100 nucleotide residues.

The term phosphorothioate oligonucleotide means an oligonucleotide or oligodeoxynucleotide in which a sulfur atom replaces one or more of the non-bridging oxygen atoms in one or more phosphodiester linkage, i.e. an oligonucleotide or oligodeoxynucleotide having one or more phosphorothiodiester linkages. Each phosphorothiodiester linkage can occur as either an Rp or Sp diastereomer. A bridging oxygen atom is an oxygen atom in a phosphodiester linkage of a nucleic acid which joins phosphorous to a sugar.

One or more of the phosphorothiodiester linkages of the phosphorothioate oligonucleotide moiety may be modified by replacing one or both of the two bridging oxygen atoms of the linkage with analogues such as NH—, $CH_2$—, or S—. Other oxygen analogues known in the art may also be used.

A phosphorothioate oligonucleotide may be a homopolymer or a heteropolymer. A homopolymer is a sequence of repeating cytidine, guanosine, adenosine, or thymidine nucleotides or other natural bases thereof. For example, SdC28 is a phosphorothioate oligonucleotide that is a homopolymer of 28 cytidine nucleotides. A heteropolymer is a sequence of alternating cytidine, guanosine, adenosine, or thymidine nucleotides, or natural bases thereof. For example, Sd(CT)10 is a phosphorothioate oligonucleotide that is a heteropolymer of 20 alternating cytidine and thymidine nucleotides.

A phosphorothioate oligonucleotide may be stereo regular, stereo non-regular or stereo random. A stereo regular phosphorothioate oligonucleotide is an phosphorothioate oligonucleotide in which all the phosphodiester linkages or phosphorothiodiester linkages polarize light in the same direction. Each phosphorous in each linkage may be either an Sp or Rp diastereomer. Phosphorothioate oligonucleotides which are created in an automated synthesizer are stereo random which means that each phosphorous atom in the phosphorothioate oligonucleotide has a 50% chance of being either an Sp or Rp diastereomer.

In a further embodiment, the phosphorothioate oligonucleotide moiety comprises a phosphorothioate oligonucleotide linked to a chemical moiety, such as a cholesteryl moiety, an intercalating agent, a cross-linker, an artificial endonuclease, a lipophilic carrier, a peptide conjugate, or a combination thereof.

In another embodiment, the phosphorothioate oligonucleotide moiety comprises a phosphorothioate oligonucleotide conjugated to a sulfated carbohydrate, a carbohydrate, or a glycan.

The present invention further provides that one or both ends of the phosphorothioate oligonucleotide of the phosphorothioate oligonucleotide moiety may be linked with the following chemical moieties: intercalating agents, such as acridine derivatives; cross-linkers, such as psoralen derivatives, azidophenacyl, proflavin, and azidoproflavin; artificial endonucleases, which comprise those conjugates whose nuclease component is able to cleave DNA specifically and nonspecifically, and acquires a specificity by covalent linkage to the oligonucleotide portion, such as metal complexes EDTA-Fe (II), o-phenanthroline-Cu(I), and porphyrin-Fe(II); and lipophilic carriers or peptide conjugates, such as long chain alcohols , phosphate esters, amino or mercapto groups, dyes or nonradioactive markers and polylysine or other polyamines.

Furthermore, one or both ends of the phosphorothioate oligonucleotide of the phosphorothioate oligonucleotide moiety may be linked with the following chemical moieties: intercalating agents, such as 2-methoxy-6-chloroacridine, methylphosphonates, methylesters, and aminoalkyls; alkylating oligonucleotides, such as acetyl; artificial endonucleases, such as amino-1-hexanolstaphylococcal nuclease, and alkaline phosphatase; peptide conjugates, such as polylysine; and terminal transferases.

Furthermore, the phosphorothioate oligonucleotide of the phosphorothioate oligonucleotide moiety may be conjugated to a carbohydrate, sulfated carbohydrate, or glycan. Such conjugates may be synthesized so as to introduce a desired specificity into the phosphorothioate oligonucleotide moiety.

In addition, the phosphorothioate oligonucleotide of the phosphorothioate oligonucleotide moiety may be combined with a cationic lipid. Examples of cationic lipids include, but are not limited to, lipofectin, dotma, and dogs.

The phosphorothioate oligonucleotide of the phosphorothioate oligonucleotide moiety may have one or more of its sugars modified or replaced so as to be ribose, glucose, sucrose, or galactose, or any other sugar. Alternatively, the phosphorothioate oligonucleotide may have one or more of its sugars substituted or modified in its 2' position, i.e. 2'allyl or 2'-O-allyl. An example of a 2'-O-allyl sugar is a 2'-O-methylribonucleotide. Further, the phosphorothioate oligonucleotide may have one or more of its sugars substituted or modified to form an α-anomeric sugar.

Furthermore, the phosphorothioate oligonucleotide of the phosphorothioate oligonucleotide moiety may have one or more of its nucleotide bases substituted or modified. Apart from the bases of adenine, guanine, cytosine, and thymine, other natural bases such as inosine, deoxyinosine, and hypoxanthine are acceptable in the phosphorothioate oligonucleotide moiety useful in the subject invention. In addition, isosteric purine 2'deoxy-furanoside analogues, 2'-deoxynebularine or 2'deoxyxanthosine, or other purine and pyrimidine analogues may also be used.

Stimulation of intracellular phosphorylation according to the subject invention may be desirable for various situations. An example of a situation in which one might want to stimulate intracellular phosphorylation would be to sensitize cells to chemotherapy. By activating either VEGF or EGF receptors on the surface of malignant cells, it may be possible for one to increase the metabolic activity of the malignant cells and thereby increase the sensitivity of the cells to chemotherapy, in one embodiment before the cells actually undergo chemotherapy.

The present invention is also directed to a method of inhibiting the formation of blood vessels in a subject which comprises administering to the subject an amount of a phosphorothioate oligonucleotide moiety of suitable length and base composition effective to inhibit VEGF molecules from binding to VEGF receptors on the surface of cells in the subject and thereby inhibit intracellular phosphorylation of tyrosine in the subject.

For purposes of the subject invention an "antiangiogenic" use describes those uses of the subject invention which result in the inhibition of the formation of blood vessels. An example of a situation in which a subject would desire an antiangiogenic effect would be when the subject suffers from a disease in which the disease causes an abnormal formation of blood vessels. The most common examples of such diseases include, but are not limited to, arteriosclerosis, atherosclerosis, cancer, diabetic retinopathy, coronary thrombosis and/or any disease resulting from neovascularization.

Accordingly, in different embodiments of this invention the subject suffers from arteriosclerosis, atherosclerosis, cancer, diabetic retinopathy, coronary thrombosis and/or any disease resulting from neovascularization.

In another embodiment of this invention the subject is a mammal, for example, a human.

The present invention also provides a method of inhibiting proliferation of cells having a malignant phenotype in a subject which comprises administering to the subject an amount of a phosphorothioate oligonucleotide moiety of suitable length and base composition effective to inhibit EGF molecules from binding to EGF receptors on the surface of cells in the subject and thereby inhibit intracellular phosphorylation of tyrosine in the subject. In one embodiment of the invention the subject is a mammal.

In one embodiment of this invention the cells are part of a tumor. As used herein the term "tumor" means any mass of malignant cells. Examples of tumors include, but are not limited to, malignant lung tumors, acute lymphatic leukemia, bladder melanoma, renal carcinoma, breast carcinoma, glioblastoma, or colorectal carcinoma. The tumor may be a tumor associated with cancer.

For purposes of the subject invention an "antiproliferative" use describes those uses of the subject invention which result in the inhibition of the proliferation of malignant cells. An example of a situation in which a subject would desire an antiproliferative effect would be when the subject suffers from a disease such as cancer in which the disease causes a proliferation of malignant cells.

In any of the methods disclosed herein the phosphorothioate oligonucleotide moiety may be administered to the subject in a pharmaceutical composition via any known mode of administration. Such means of administration are well known to those skilled in the art and include, but are not limited to, topical administration, parenteral administration, oral administration, or intraperitoneal, intravenous, intratracheal, intramuscular, or subcutaneous injection. Administration of the phosphorothioate oligonucleotide moiety may be effected continuously or intermittently. Administration may also be in combination with cationic lipids or other carriers.

A pharmaceutical composition comprising a phosphorothioate oligonucleotide moiety described herein may include any of the known pharmaceutical carriers. Examples of suitable pharmaceutical carriers include any of the standard pharmaceutically accepted carriers to one of ordinary skill in the art. Examples of such pharmaceutical carriers include, but are not limited to, phosphate buffered saline solution, water, emulsions such as oil/water emulsions or a triglyceride emulsion, various types of wetting agents, tablets, coated tablets and capsules. A suitable pharmaceutically acceptable carrier may be selected taking into account the chosen mode of administration.

An effective amount of a pharmaceutical composition comprising a phosphorothioate oligonucleotide moiety is that amount which is effective to bring about the desired effect in the subject. Accordingly, an effective amount will depend on various factors known to those of ordinary skill in the art. Such factors include, but are not limited to, the size of the subject and the degree to which the disease from which the subject suffers has progressed. The effective amount will also depend on whether the phosphorothioate oligonucleotide moiety is going to be administered to the subject in a single dosage or periodically over a stretch of time.

This invention will be better understood from the Examples in the "Experimental Details" Section which follows. However, one skilled in the art will readily appreciate that the specific methods and results discussed therein are merely illustrative of, and are not intended to, nor should they be construed to, limit the invention as described more fully in the claims which follow thereafter.

EXPERIMENTAL DETAILS

Materials and Methods

Phosphorothioate Oligodeoxynucleotides

All oligonucleotides were synthesized by standard phosphoramidite chemistry and purified as described by Tonkinson and Stein [7]. The SdC28 and SdC18 have been described [2]. The remaining oligodeoxynucleotides used in these studies had the following sequences: #2 (G9CCGGGCCAT), #2T (G9TTGGGTTAT) and G6T12. Oligodeoxynucleotides were diluted in sterile phosphate-buffered saline (PBS) to a concentration of 1 mM, aliquoted and stored frozen.

Cell Lines, Reagents and Growth Assays

The NIH 3T3, KB and DU145 cell lines were obtained from the American Type Culture Collection. The GBM-18 cell line used in the animal studies was derived from a patient with Stage IV glioblastoma multiforme. These cells show a high level of tumorigenicity in mouse xenografts as described [8]. C441, a NIH 3T3 cell line transfected with a chimeric mouse flk-1/human cfms receptor [9] was maintained in Dulbecco's modified Eagle's medium (DMEM) containing 10% calf serum (CS). The tumor lines, KB, DU145 and GBM-18 were grown in RPMI 1640 supplemented with 1 mM glutamine, antibiotics and 10% fetal calf serum (FBS). The anti-flk-1 monoclonal antibodies (MAbs) were raised against a soluble flk-1 receptor using the procedure described by Rockwell et al. [10]. For growth assays confluent KB cells were plated in 6 well plates (10,000 cells/well) in the presence or absence of either 2 µM SdC28, 2 µM #2T or 2 µM SdG6T12 oligodeoxynucleotides. After 72 hours the medium was removed and the cells were processed at room temperature as follows: cells were fixed with 1% neutral buffered formalin for 15 minutes, permeabilized with cold 70% ethanol for 15 minutes and then incubated with Giemsa stain for 30 minutes. After extensive washing with distilled water, cells were examined by light microscopy and morphologically assessed.

Phosphorylation Assays and Western Blotting

The phosphorylation assays and Western blot analyses with C441 and tumor cell lines were described previously [10]. Briefly, subconfluent cell are serum starved in DMEM containing 0.5% CS (C441) or RPMI with 0.5% bovine serum albumin (BSA) (KB and DU145) for 24 hours. For these neutralization assays, cells were prebound with 2 µM of the oligodeoxynucleotides indicated in serum free medium for 15–30 minutes at room temperature and then stimulated with human recombinant forms of the appropriate ligand, 20 ng/ml VEGF (Peprotech) or 10 ng/ml EGF (Sigma), for 15 minutes. Where indicated, cells were subjected to a cold PBS wash prior to the addition of VEGF. After a 15 minute incubation cells were washed, lysed and subjected to Western blot analysis for phosphoprotein detection with an anti-phosphotyrosine MAb (UBI). These analyses were performed either with total cell lysates (KB cells) or lysates immunoprecipitated with an anti-fms polyclonal antibody (C441 cells) or an anti-flk-1 MAb, DC101, (DU145 cells), that is cross reactive with human VEGF receptor forms [10].

Immunofluorescent Detection of Oligodeoxynucleotide Binding

For binding studies, C441 cells were removed with 2 mM EDTA in PBS, washed with cold Hanks balanced salt solution supplemented with 1% BSA (HBSS-BSA) and then resuspended in 100 µl of the same buffer at a concentration of 1 million cells per sample. Where indicated, cells were incubated with 2 µM oligodeoxynucleotides of 10 µg/ml heparin. After a 30 minute incubation on ice, cells were washed and reincubated for 30 minutes with 10 µg of the appropriate MAb. After washing, a 1:40 dilution of goat anti-mouse IgG conjugated to FITC (TAGO) was added for a final 30 minute incubation on ice. Cells were then analyzed on a Coulter Epics Elite Cytometer. Nonspecific binding was determined from samples incubated with oligodeoxynucleotide alone and an irrelevant anti-gp75 MAb (TA99).

Animal Tumor Assays

Animal studies were conducted with groups containing 5–10 athymic nude mice (nu/nu; Charles River Labs). Treatments were initiated 7 days post implantation of 1–2 million GBM-18 cells/mouse. Animals were injected either intraperitoneally with MAb DC101 (200 µg antibody/mouse) or subcutaneously with oligodeoxynucleotides SdC28 and #2 (200 µl of a 1 µM solution in PBS/mouse) twice weekly for three weeks. PBS treated mice served as controls. Tumor size was measured twice weekly with a caliper and tumor volume was calculated by the formula V=n/6×larger diameter×(smaller diameter)$^2$ [11].

RESULTS

Oligodeoxynucleotides Block VEGF Induced Receptor Activation

In these studies we examined non-specific oligodeoxynucleotides for their ability to perturb two cell surface protein tyrosine kinase receptors, EGFR and flk-1. To address the interactions with a specific cell surface expressed protein, phosphorothioate oligodeoxynucleotides were assayed for their effects on the activation of the flk-1/fms receptor by its cognate ligand VEGF in the C441 transfected cell line. In these assays, ligand was added to cells that were prebound with oligodeoxynucleotide either before or after a PBS wash. The results (FIG. 1) indicate that phosphorothioate oligodeoxynucleotides have the capacity to abrogate the VEGF-induced receptor phosphorylation of unwashed cells (FIG. 1, lanes 5&6) to the level of unstimulated cells (FIG. 1, lane 4). The ability of the oligodeoxynucleotides to do this is comparable to that of the neutralizing anti-flk-1 MAb, DC101 [10]. The potency of the inhibition observed here, however, can be attributed at best, in part, to the fact that oligodeoxynucleotides bind VEGF in solution [5]. However, the data also show that oligodeoxynucleotides remain bound to the C441 cell surface after washing, and exert a partial inhibition of receptor activation (FIG. 1, lanes 1&2) relative to controls (FIG. 1, lanes 3&7). It was also shown that oligodeoxynucleotide #2 elicited a more inhibitory effect than SdC28 on washed cells. Inhibition was also observed for two additional oligodeoxynucleotides, #2T and SdG6T12 (a tetraplex former), when assayed under the same conditions but the oligodeoxynucleotides alone had no effect on receptor activation when assayed in the absence of ligand (date not shown).

Oligodeoxynucleotides Elicit Agonist and Antagonist Effects on EGFR Activity

Figure 2B:
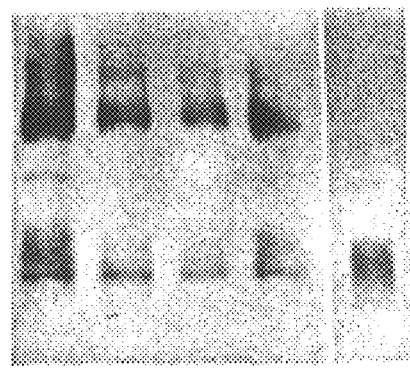
FIG. 2B: Effect of oligodeoxynucleotides on EGF-induced activation of EGFR. The level of receptor phosphorylation is shown for EGF (10 ng/ml) stimulated cells preincubated without oligodeoxynucleotide (lane 1) or with 2 μM of the oligodeoxynucleotides SdC28 (lane 2), #2T (lane 3) and G6T12 (lane 4) versus unstimulated cells (lane 5).
Figure 4A:
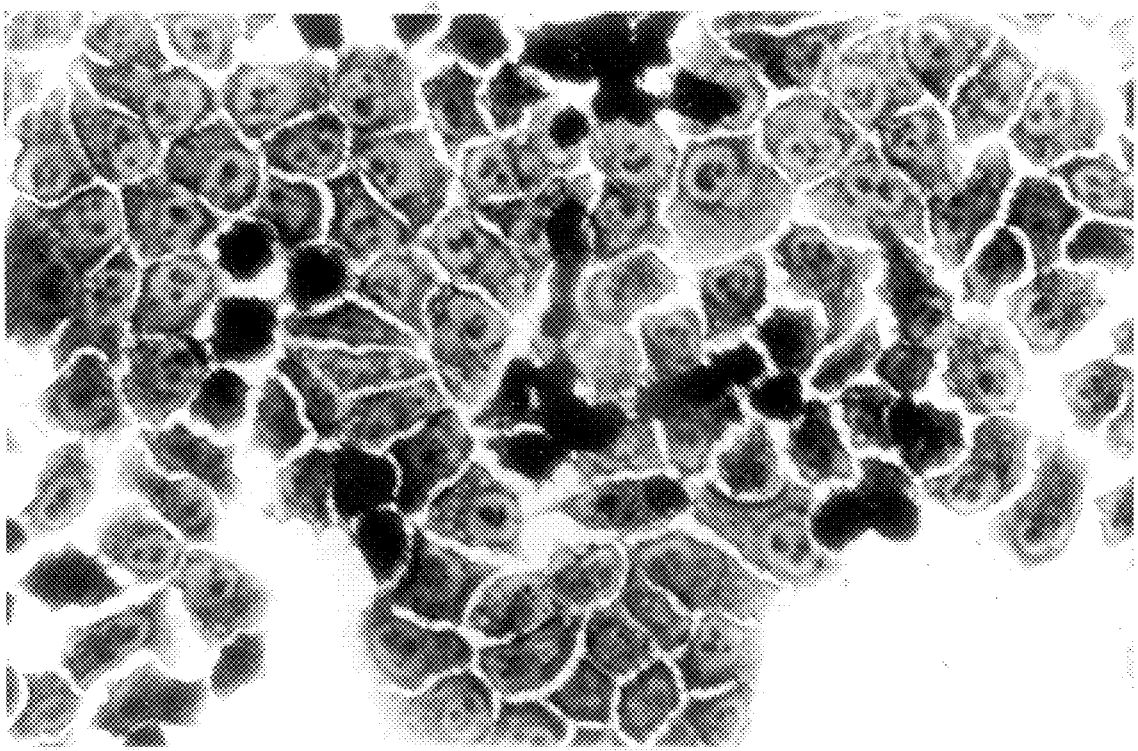
Figure 4B:
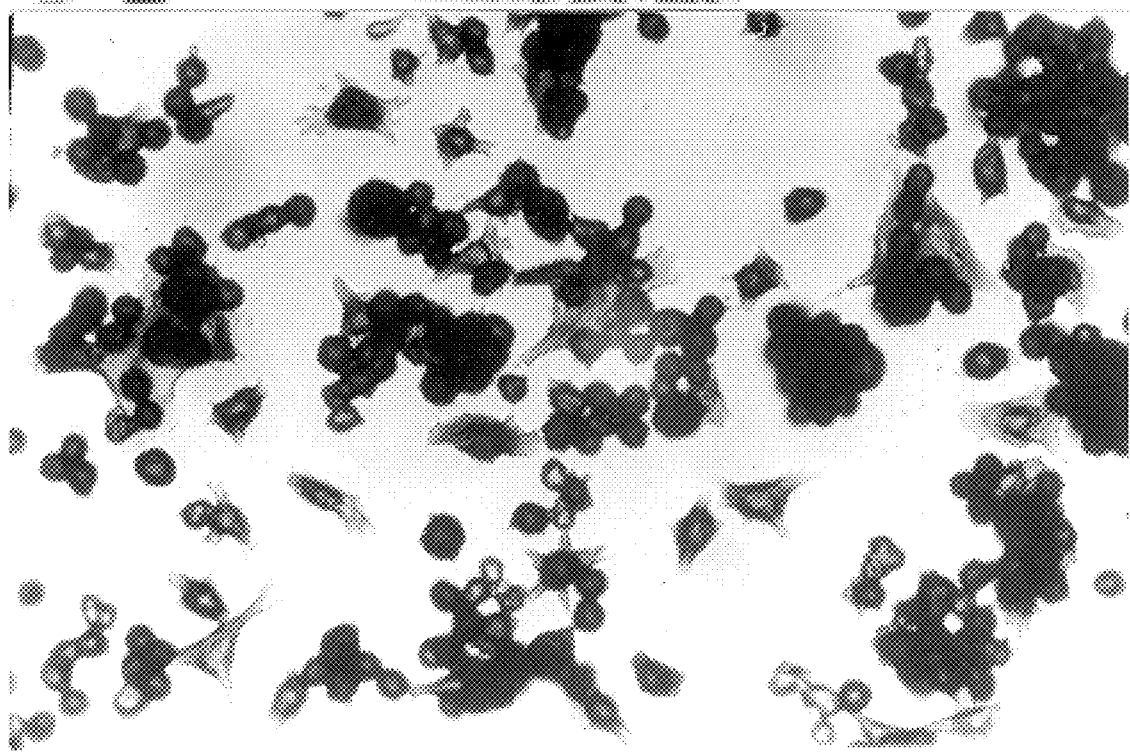

Similar studies were performed on the activation of overexpressed EGFR in the epidermoid tumor cell line (KB). Because oligodeoxynucleotides do not appear to bind to EGF [5], these experiments preclude the possibility that perturbations of receptor kinase activity reflect ligand-oligodeoxynucleotide interactions. These results indicate that oligodeoxynucleotides can either act as agonists or antagonists of EGFR activation depending on the presence or absence of ligand (FIG. 2). In the absence of EGF, increased phosphoprotein patterns were observed when KB cells were incubated with either the SdC28, #2T or SdG6T12 oligodeoxynucleotide alone (FIG. 2A). Conversely, these oligodeoxynucleotides, together with #2, elicited a differential inhibitory effect on EGFR signaling patterns in the presence of ligand relative to the control (FIG. 2B). Verification that the phosphorylated bands corresponded to EGFR was obtained by reprobing the blots with an anti-receptor polyclonal antibody (UBI) (data not shown).

The agonist effects of oligodeoxynucleotides were also obtained with the prostatic tumor line DU145 (FIG. 3A). Levels of phosphoproteins were differentially increased subsequent to oligodeoxynucleotide treatment (SdC28 versus #2). The phosphoproteins were immunoprecipitated by the anti-flk-1 MAb Dc101 from lysates of cells assayed in the absence of EGF. Surprisingly, a 170 kDa phosphorylated band obtained from EGF stimulated cells treated with oligodeoxynucleotide #2 showed reactivity with an anti-EGFR antibody (FIG. 3B). These results indicated that oligodeoxynucleotide interactions at the cell surface can lead to a receptor activation that mimics ligand binding.

In addition these results also demonstrated that EGF mediates an association of its activated receptor with non-phosphorylated proteins immunoprecipitated by anti-flk-1 MAbs (data not shown).

Oligodeoxynucleotides Induce Changes in Cell Morphology

To determine whether cell surface perturbations induced by phosphorothioate oligodeoxynucleotides were manifested as morphological effects on cells in culture, KB cells were grown in the presence of 2 μM oligodeoxynucleotides over 72 hours. A dramatic change in cell morphology was observed in the oligodeoxynucleotide treated cells (FIGS. 4A–D). Unlike the cobblestone appearance of the control cells (FIG. 4A) the SdC28 treated cells (FIG. 4B) showed enlarged nuclei and extensive bleebing whereas cells cultured with #2T (FIG. 4C) and SdG6T12 (FIG. 4D) were smaller, poorly attached and contained dense chromatin material.

Oligodeoxynucleotides Block Cell Surface Receptor Binding By Anti-flk-1 MAbs

Figure 5A:
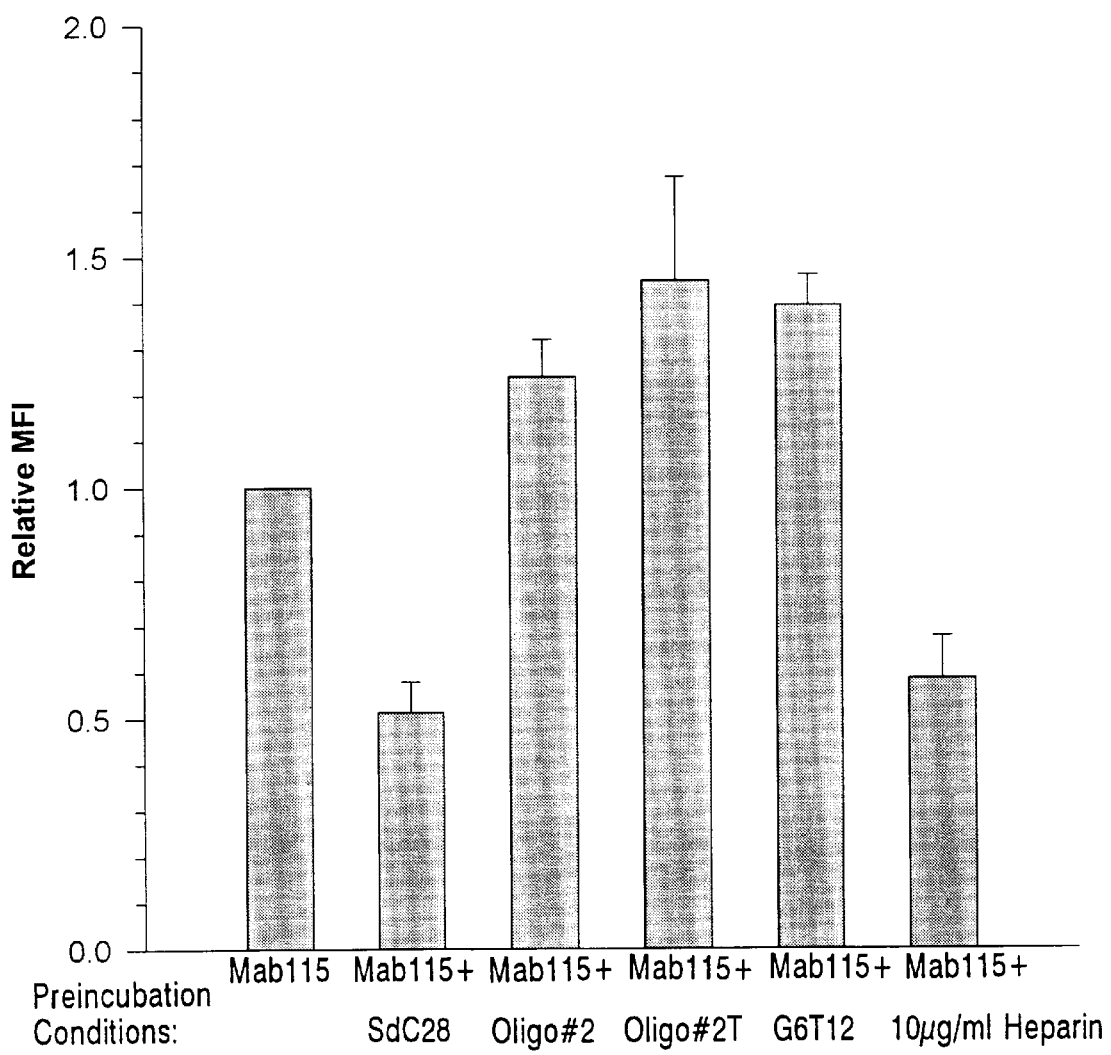
FIGS. 5A–5C: FACS analysis of phosphorothioate oligodeoxynucleotide blockade of MAb binding to cell surface targets. Shown is the binding of the anti-flk-1 MAbs 115 (FIG. 5A), 73 (FIG. 5B) and DC101 (FIG. 5C) to C441 cells preincubated with either 2 μM of the oligodeoxynucleotides SdC28, #2, #2T, G6T12 or 10 μg/ml heparin or without oligodeoxynucleotide. All incubations were performed on ice to prevent flk-1 receptor internalization. The specific preincubation conditions used for each MAb binding experiment are indicated in the appropriate figure. Each graph represents the mean fluorescent intensity (MFI) of MAb binding to cells pretreated with oligodeoxynucleotide or heparin relative to the binding determined for cells incubated without competitors (MFI=1). The data are averages of the relative MFI (+/− SEM) from at least 3 independent experiments. With the exception of MAb 115 binding to #2 treated cells in FIG. 5A, a statistical analysis (t-test) of the data showed that MAb binding to cells pretreated with either oligodeoxynucleotide or heparin were significantly different ($p<0.05$) from their respective controls.
Figure 5B:
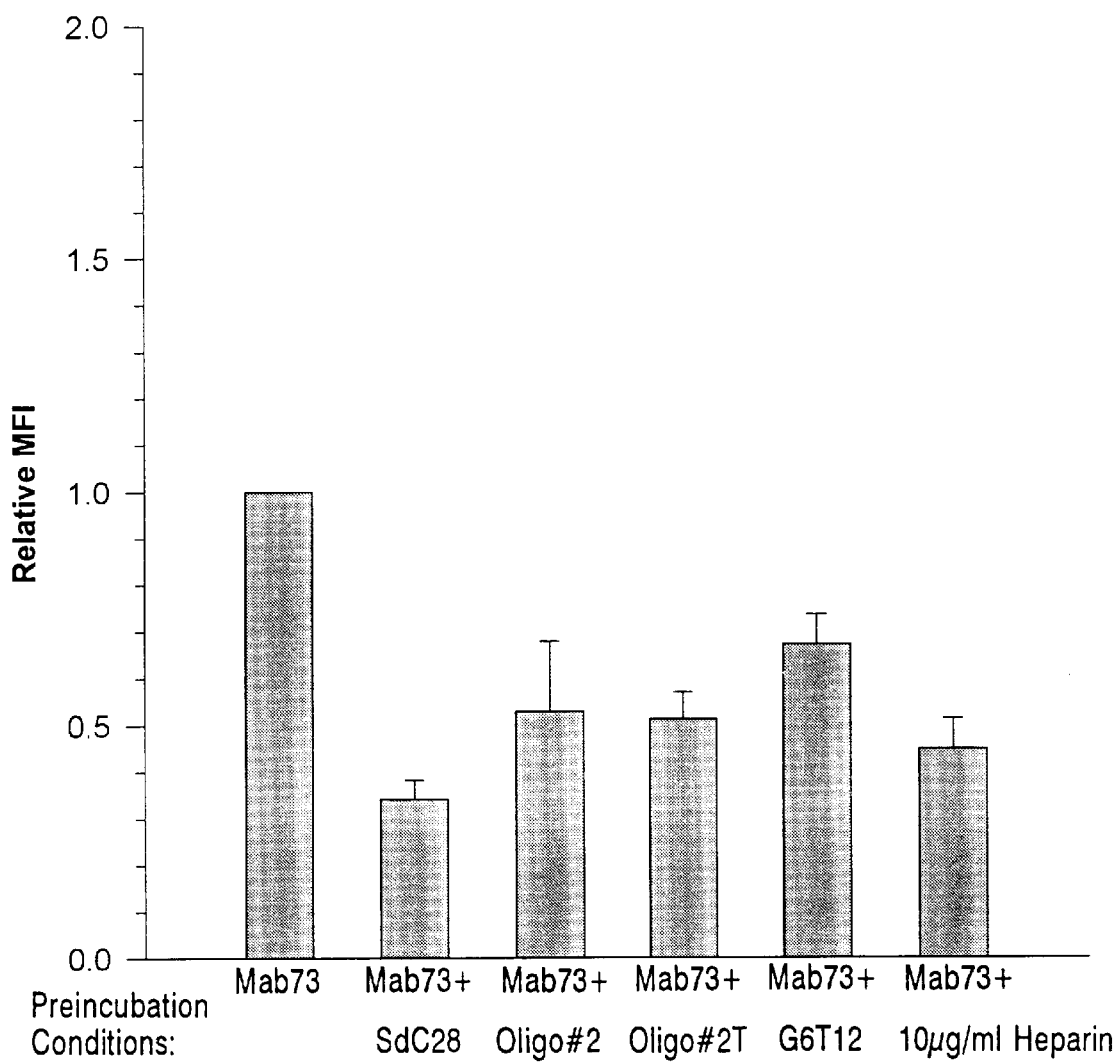
Figure 5C:
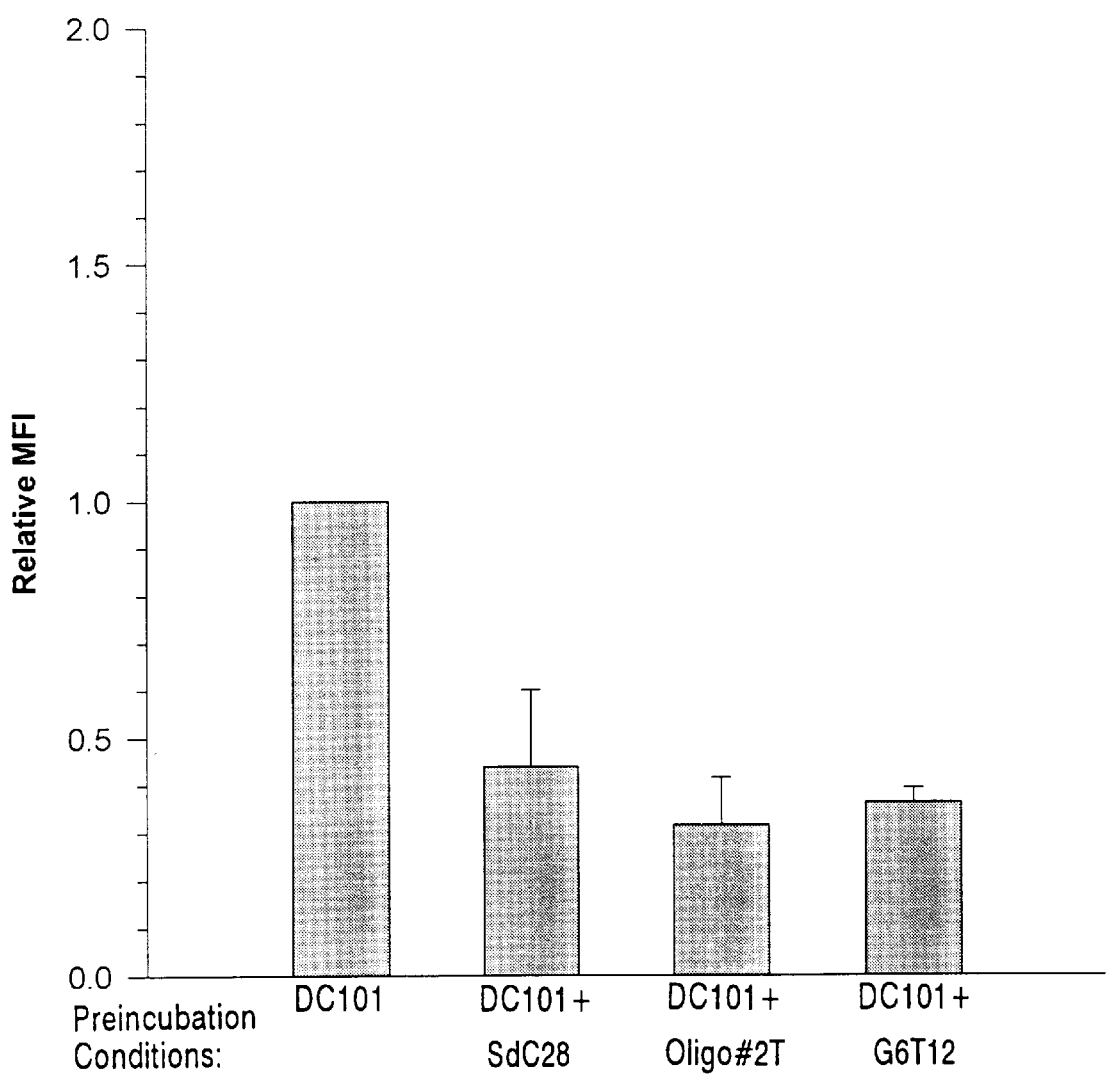
Figure 6B:
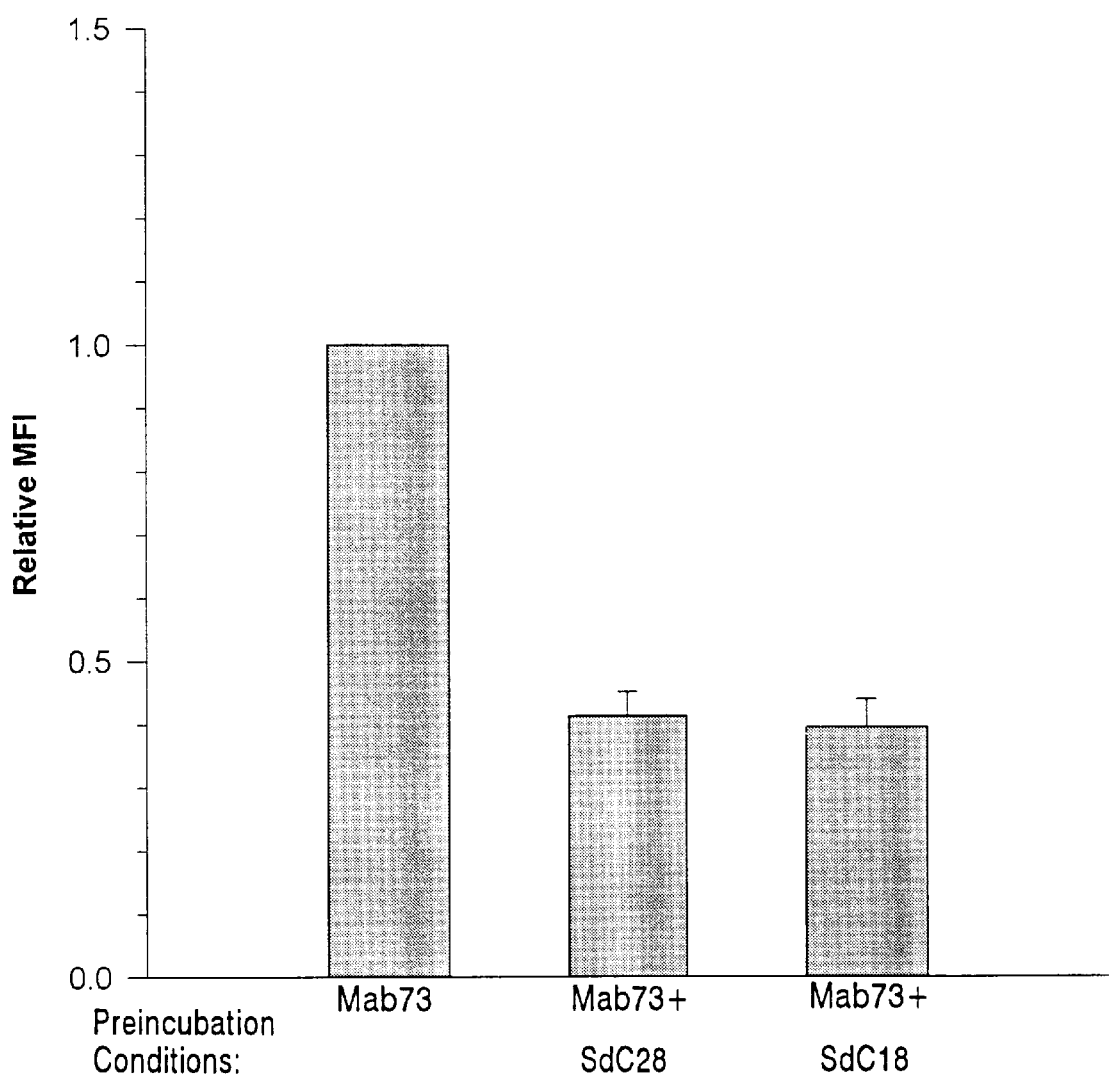

A more direct demonstration of the interactions of oligodeoxynucleotides with cell surface proteins was obtained from FACS analyses showing oligodeoxynucleotide-induced blockade of the binding of three anti-flk-1 MAbs that possess different affinities for their receptor [10]. The demonstration that the observed non-sequence specific effects were exerted at the cell surface was insured by performing assays under conditions that minimized receptor internalization. These experiments (FIGS. 5A–C) indicate that oligodeoxynucleotides vary in their effects on MAb binding to C441 cells. The mean fluorescent intensity of MAb binding to oligodeoxynucleotide treated cells relative to cells bound to MAb alone is shown in FIG. 5. SdC28 elicited a partial block of the binding of MAbs 115 (FIG. 5A), 73 (FIG. 5B) and DC101 (FIG. 5C) to C441 cells whereas the #2, #2T and SdG6T12 oligodeoxynucleotides also inhibited MAb DC101 binding to the same extent. Binding of MAb 73 was inhibited to a lesser extent. Conversely, #2T and SdG6T12 enhanced MAb 115 to cell surface flk-1. Data on the inhibition of MAbs 115 and 73 binding by 10 μg/ml heparin has been included as a comparison with similar effects of phosphorothioate oligodeoxynucleotides. The greater inhibition (an approximate 40% decrease) of MAb 115 binding observed with SdC28 relative to SdCl8 (FIG. 6A) is evidence that blockade of binding is determined by oligodeoxynucleotide length. This differential effect was not obvious with MAb 73 (FIG. 6B) which was more sensitive to inhibition of binding by both oligodeoxynucleotides.

Oligodeoxynucleotide SdC28 Suppresses Tumor Growth

Figure 7:
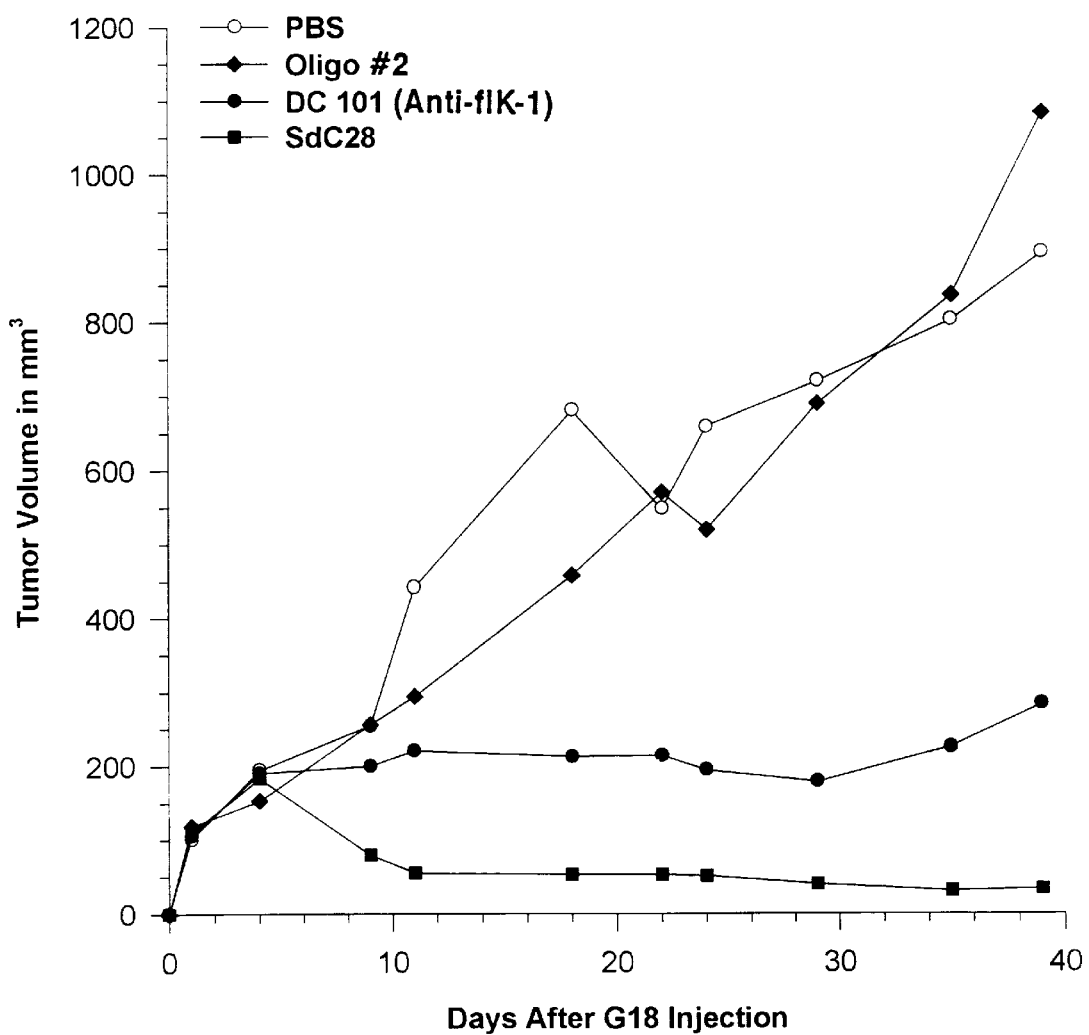
FIG. 7: Effect of phosphorothioate oligodeoxynucleotides SdC28 and #2 on established tumor growth in a mouse model of human glioblastoma. Treatments were initiated 7 days post implantation of GBM-18 cells. Results are plotted as the tumor volume over time for each treatment: PBS (open circles), oligodeoxynucleotide #2 (closed diamonds), DC101 (closed circles), and oligodeoxynucleotide SdC28 (closed squares). A statistical analysis of a regression of the data points for each animal group over time (regressed line not shown on graph) showed that the rate of tumor growth (slope of each regression) for SdC28 and MAb DC101 was significantly different from the PBS control ($p<0.001$).
Figure 8:
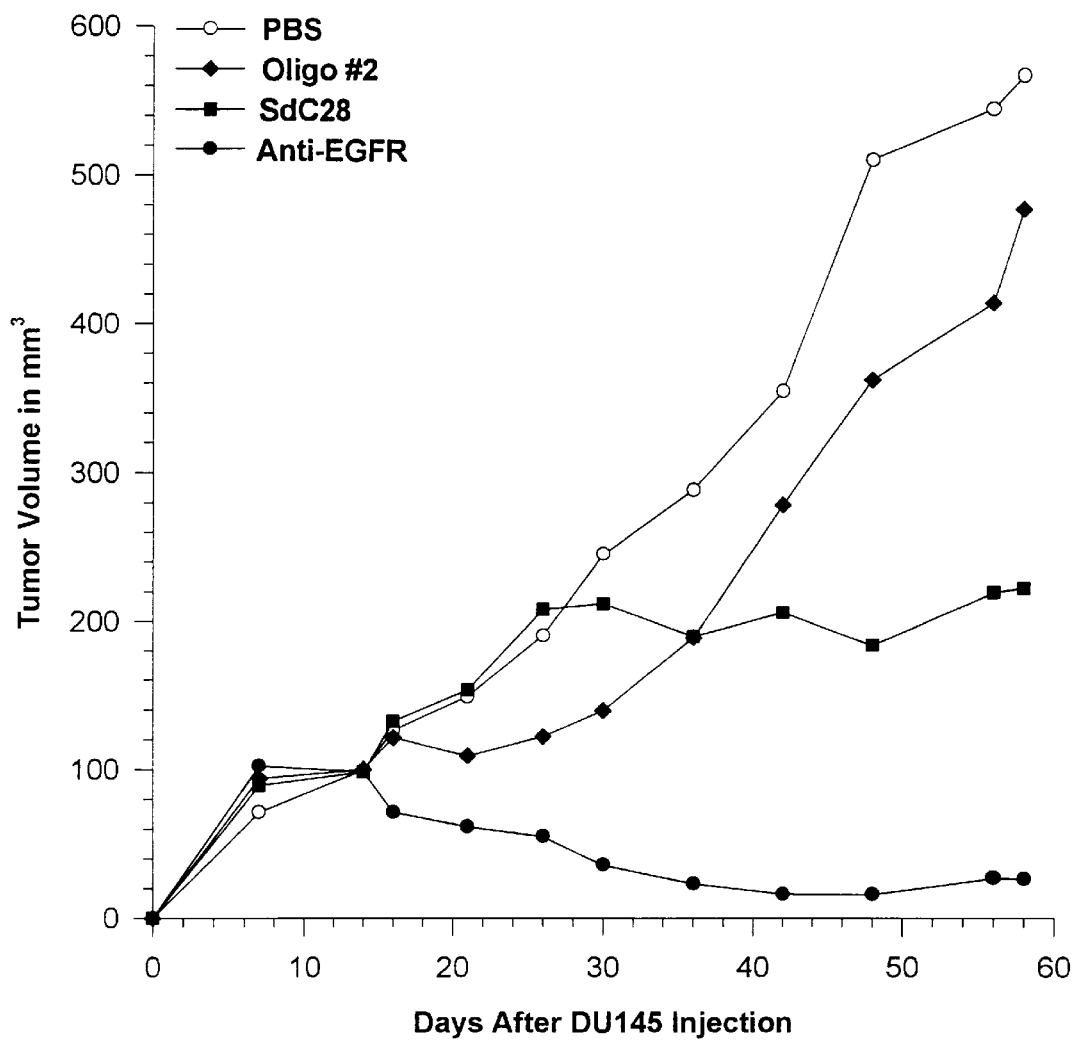
FIG. 8: Effect of phosphorothioate oligodeoxynucleotides SdC28 and #2 on established prostatic tumor growth in a mouse model. Treatments were initiated 7 days post implantation of DU-145 cells. Results are plotted as the tumor volume over time for each treatment: PBS (open circles), oligodeoxynucleotide #2 (closed diamonds), Anti-EGFR MAb (closed circles), and oligodeoxynucleotide SdC28 (closed squares). A statistical analysis of a regression of the data points for each animal group over time (regressed line not shown on graph) showed that the rate of tumor growth (slope of each regression) for SdC28 and Anti-EGFR MAb was significantly different from the PBS control ($p<0.001$).

To assess their potential therapeutic efficacy, SdC28 and #2 were examined for their ability to suppress the growth of human glioblastoma xenografts in nude mice (FIG. 7). These studies included an anti-flk-1 MAb (DC101) which has been shown to induce a significant inhibition of glioblastoma growth in this tumor model [8]. These results indicate that the SdC28 oligodeoxynucleotide and MAb DC101, but not #2, induced a significant inhibition (p<0.001) of tumor growth relative to that of the PBS control. There was no evidence of toxicity as determined by body weight and food intake. Although the effects of MAb DC101 can presumably be attributed to an inhibition of tumor angiogenesis [8] it is difficult to ascertain precisely the basis for the oligodeoxynucleotide suppression of tumor growth in vivo due to the pleiotropic effects the oligodeoxynucleotide displays in vitro. Results from cell proliferation assays showed that 2 μM SdC28 inhibited endothelial cell (HUVEC) growth to 30% of control values but had no effect on the glioblastoma cell line, GBM-18 (data not shown).

Discussion

The results presented show that phosphorothioate oligodeoxynucleotides interact non-sequence-specifically with cell surface expressed proteins, especially with certain protein tyrosine kinase receptors and their downstream signaling pathways. These studies also indicate that oligodeoxynucleotides designed without sequence-specific targets have the capacity to elicit changes in cell morphology and suppress tumor growth. The variations in the cell surface binding efficiencies among the oligodeoxynucleotides may be attributed to sequence, length and to the differential affinities of anti-flk-1 MAbs for their targets. Thus, an antibody with a higher relative affinity (MAb 115>MAbs 73>DC101) for its target may readily displace a competitor from binding sites on the cell surface. The fact that inhibition of MAb binding and receptor phosphorylation is still evident after washing cells prebound with oligodeoxynucleotides suggests that phosphorothioate oligodeoxynucleotides are bound with high affinity to the cell surface at concentrations sufficient to perturb cellular activities. The data from the MAb 115 binding studies and previous reports [2] suggest that longer oligodeoxynucleotides (e.g., SdC28 versus SdCl8) may bind more avidly to proteins. However, the similarity in sensitivity of MAb 73 to binding inhibition by SdC28 and SdC18 also suggests that the effect of oligodeoxynucleotide length on MAb binding may vary considerably depending on the affinity of the ligand for its receptor. The sensitivity of the flk-1/fms to inhibition by phosphorothioate oligodeoxynucleotides resembles the previously demonstrated block of this receptor's activation by heparin [9] and demonstrates that phosphorothioate oligodeoxynucleotides have behavioral properties similar to several naturally occurring polyanions, including heparin [3,5]. Other studies have shown that heparin can trigger phosphorylation of EGFR [13]. In addition, phosphorothioate oligodeoxynucleotides with specific sequences have been shown to elicit nonantisense effects; for example, constructs with four contiguous guanine residues (G quartet) displays a high affinity for proteins [1] and CpG motifs can induce cellular immune responses [12]. The perturbation of the EGF and flk-1/fms receptors is also reminiscent of the sensitivity of the bcr-abl kinase to oligodeoxynucleotide treatment [6]. It is not clear whether the observed changes in phosphorylation is solely due to a direct binding of oligodeoxynucleotide to receptor since it may also be true that interactions with associated kinases or phosphatases can lead to altered phosphoprotein patterns. Furthermore, it is difficult to predict which of the various effects elicited by the oligo SdC28 in vitro is responsible for its potent suppression of glioblastoma tumor growth in vivo. Given the diversity of their behavior in vitro, it is reasonable to assume that phosphorothioate oligodeoxynucleotides utilize multiple mechanisms of action to produce their antiproliferative effects in vivo.

The fact that the events described above result from nonantisense interactions should not detract from the therapeutic potential of phosphorothioate oligodeoxynucleotides as anticancer reagents. The fact that a phosphorothioate oligodeoxynucleotide appears to function in a sequence-specific manner, and can downregulate targeted expression does not preclude its synchronous capacity for non-sequence specificity. Indeed, stringent criteria must be established in order to determine whether an observed biological effect results from a true antisense mechanism. Many biological endpoints attributed to antisense activity may, in reality, be the result of the interaction of nucleic acid and protein, as shown herein.

REFERENCES:

1. Stein, C. A., *Nature Med.* 1, 119–1121 (1995).
2. Stein, C. A. and Cheng, Y.-C. *Science* 261, 1004–1012 (1993).

3. Khaled, Z., et al. *Clin. Cancer Res.* 1, 113–122 (1995).
4. Yakubov, L., et al. *J. Biol. Chem.* 268, 18818–18823 (1993).
5. Guvakova, M. A., et al. *J. Biol. Chem.* 270, 2620–2627 (1995).
6. Bergan, R. C., et al. *Antisense Res.* Dev. 5 (1995).
7. Tonkinson, J. L., and Stein, C. A. *Nucleic Acids Res.* 22, 4268–4275 (1994).
8. Rockwell, P., and Goldstein, N. I., *Mol. Cell Diff.* 3, 315–335 (1995).
9. Tessler, S., *J. Biol. Chem.* 269, 12456–12461 (1994).
10. Rockwell, P., *Mol. Cell. Diff.* 3, 91–109 (1995).
11. Baselga, J., *J. Natl. Cancer Inst.* 85, 1327–1333 (1993).
12. Krieg, A. M., *Nature* 374, 546–549 (1995).
13. Borowski, P., et al., *J. Biochem.* 115, 825–829 (1994).

What is claimed is:

1. A method of inhibiting proliferation of cells having a malignant phenotype in a subject which comprises administering to the subject an amount of a phosphorothioate oligonucleotide moiety of suitable length and base composition effective to inhibit EGF molecules from binding to EGF receptors on the surface of cells in the subject and thereby inhibit intracellular phosphorylation of tyrosine in the subject.

2. A method according to claim 1, wherein the cells are part of a tumor.

3. A method according to claim 1, wherein the subject is a mammal.

* * * * *